United States Patent [19]
Iwasa et al.

[11] 4,059,491
[45] Nov. 22, 1977

[54] DILUENTS FOR RUBELLA VIRUS HEMAGGLUTINATION-INHIBITION TEST

[75] Inventors: Susumu Iwasa, Kyoto; Isamu Yoshida, Takatsuki, both of Japan

[73] Assignee: Takeda Chemical Industries, Ltd., Osaka, Japan

[21] Appl. No.: 764,058

[22] Filed: Jan. 31, 1977

[30] Foreign Application Priority Data
Feb. 2, 1976    Japan ................................. 51-10474

[51] Int. Cl.² .................... G01N 33/16; C12K 1/04
[52] U.S. Cl. ....................... 195/103.5 A; 23/230 B; 195/103.5 V; 424/12
[58] Field of Search ................. 23/230 B; 424/11, 12; 252/408; 195/103.5 A, 103.5 V

[56] References Cited
U.S. PATENT DOCUMENTS
3,516,794   6/1970   Murty et al. ..................... 23/253 X OTHER PUBLICATIONS
Journal of Immunology, 104, 818 (1970).

Primary Examiner—R.E. Serwin
Attorney, Agent, or Firm—Burgess, Ryan and Wayne

[57] ABSTRACT

In the rubella virus hemagglutination-inhibition test, the hemagglutination-inhibition antibody titers of the test sera can be determined with accuracy and high sensitivity by employing a novel diluent, which contains N-2-hydroxyethylpiperazine-N'-2'-ethanesulfonic acid in a low concentration and which is free from calcium ion, for the dilution of the rubella virus hemagglutinating antigen and of the test sera.

16 Claims, No Drawings

DILUENTS FOR RUBELLA VIRUS HEMAGGLUTINATION-INHIBITION TEST

The present invention relates to diluents for rubella virus hemagglutination-inhibition test.

The hemagglutination-inhibition (hereinafter briefly referred to as HI) test for rubella virus is an important tool in serological diagnosis because of its comparatively high sensitivity, expedience and convenience in use as compared to other diagnostic procedures for rubella virus, such as neutralization, complement fixation, fluorescent antibody and other tests.

Heretofore, in such rubella virus HI tests, the three reactants, rubella virus hemagglutinating antigen (hereinafter briefly referred to as rubella virus HA antigen), test serum and erythrocytes have been used as previously diluted with the same type of diluent, and various diluents for this purpose are known. Each of the known diluents, however, has its own disadvantages. Currently the veronal buffer solution is most commonly employed. However, the sensitivity of the rubella virus HI test is about 10 times higher in the pH range of about 6.0 to 6.5 than at pH 7.2, the pH level established by veronal buffer [Journal of Immunology 104, 818(1970)]. Thus, use has often been made of diluents buffered by N-2-hydroxyethylpiperazine-N'-2'-ethanesulfonic acid (hereinafter referred to briefly as HEPES) which has a high buffer capacity in the pH range of 6.0 to 6.5 and which helps produce a stable, well-defined erythrocyte agglutination pattern. This diluent contains not only HEPES in a molar concentration of 0.025 but also NaCl in a molar concentration of 0.14, 1% (weight/volume; also hereinafter) of bovine serum albumin, 0.00025% of gelatin and 0.001 molar concentration of $CaCl_2$, and each of these ingredients have been considered to be essential because of their invariable major influences upon the sensitivity of the HI reaction, the stability of the resultant erythrocyte agglutination pattern and the distinctness of the end-point of the reaction. Generally the rubella virus HA antigen is rapidly inactivated on dilution with a diluent, and in the employment of said HEPES buffer, as it is the case with other buffers, one is not in the position to use a stored previously diluted rubella virus HA antigen fluid but must dilute the antigen to the prescribed concentration of 4 hemagglutinating (HA) units just before conducting the reaction with a test serum. Moreover, the inactivation of the HA antigen takes place even on such an occasion, thus interfering with an accurate assessment of the end-point of the HI reaction of rubella HI antibody in the test serum, with the result that the HI antibody titer thus determined is neither accurate nor reproducible.

Under the technical circumstances described above, the present inventors have unexpectedly found that the inactivation of rubella virus HA antigen in a system of rubella virus HA antigen diluted with HEPES buffer is dependent upon, and results from, the concentration of HEPES and the presence of $CaCl_2$. The present invention has been developed on the above-mentioned surprising finding and its principal object is to provide a novel diluent for rubella virus HA antigen and for rubella virus HI test sera which is conducive to a sustained stability of the HA activity of rubella virus HA antigen and does not have any adverse effect upon the antigen-antibody reaction. Another object of the present invention is to provide a method for a rubella virus HI test which comprises employing the said novel diluent in combination with a diluent for erythrocytes which is such that it permits the HI reaction with high sensitivity and gives a stable and distinct erythrocyte agglutination pattern, thereby allowing the rubella virus HI antibody titer in the test serum to be determined with accuracy and high sensitivity. Other objects will be made clear from the description and claims presented hereinafter.

The diluent of the present invention for rubella virus HA antigen and for rubella virus test sera is a novel composition which contains HEPES in a molar concentration from about 0.001 to about 0.01 and NaCl, the pH of which is in the range of about 6.0 to about 7.5, and which is free from calcium ion. This diluent is essentially characterized by its containing HEPES in a low concentration, i.e. the molar concentration from about 0.001 to about 0.01 and its being free from the calcium ion. By means of this novel composition it is possible to preclude inactivation of rubella virus HA antigen almost completely and thereby to ensure an effective use of stored previously diluted HA antigen. It is particularly advantageous that this diluent contains HEPES in a molar concentration from about 0.004 to about 0.006 and has a pH in the range of about 6.0 to about 6.5, particularly near 6.2. As to the concentration of NaCl in this diluent, generally it is preferably in a molar concentration from about 0.05 to about 0.3. Particularly where a rubella virus HI test is performed with the employment of fresh erythrocytes, NaCl is preferably contained in a molar proportion of about 0.14 to about 0.15 mole. It is preferable that this diluent further contains albumin, which preferably is serum albumin, especially bovine serum albumin. Normally the concentration of albumin is preferably in the range of about 0.05 percent to about 1 percent.

According to this invention use may be made of the diluent for the erythrocytes which contains calcium ions in a sufficient concentration to let the rubella virus HI reaction take place with high sensitivity and HEPES in a sufficient concentration to let the diluent display high buffer capacity, thus helping produce a stable, well-defined erythrocyte agglutination pattern. The concentration of HEPES in this diluent may be in the range of about 0.01 mole to about 0.05 mole and, preferably, about 0.025 mole. The concentration of $CaCl_2$ is in the range of about 0.0005 mole to about 0.01 mole, preferably about 0.002 mole. The pH of the diluent is in the range of about 6.0 to about 6.5, preferably about 6.2. Generally the concentration of NaCl in this diluent is preferably in the range of about 0.05 mole to about 0.3 mole and, where fresh erythrocytes are employed, the range of about 0.14 mole to about 0.15 mole is particularly desirable. This diluent preferably contains gelatin, the concentration of which may be in the range of about 0.001 percent to about 0.01 percent, preferably about 0.005 percent.

The test serum for use in the practice of this invention may be any type of serum provided that it lends itself to the determination of rubella virus HI antibodies. Thus, for example, the sera of warm-blooded animals such as human beings, cattle, rabbits, rats and the like may be mentioned. Particularly, the test serum may be the human serum taken for the purpose of determining the titer of rubella virus HI antibodies.

It is preferable that, prior to dilution with the diluent according to this invention, such a test serum be subjected to a pretreatment adapted to remove or inactivate the non-specific inhibitors of agglutination occurring in the serum. As examples of said pretreatment may be mentioned adsorption on kaolin, extraction with acetone, precipitation with heparine-$MnCl_2$, etc. Particularly advantageous is the method wherein phospholipase C is permitted to act upon the test serum to inactivate its non-specific inhibitors of agglutination.

The erythrocytes may be any erythrocytes which lend themselves to agglutination with rubella virus HA antigen. Thus, for example, the erythrocytes of fowls such as one-day-old chicks, geese, pigeons, quails, etc. are advantageous. Such erythrocytes may be fresh cells or fixed erythrocytes. The fixed erythrocytes are preferably formalinized erythrocytes. For example, the formalinized erythrocytes of one-day-old chicks described in e.g. Japanese Patent Publication No. 37724/1975 may be put to use with advantage.

This invention, in one aspect thereof, provides a method for the rubella virus HI test, which comprises admixing a rubella virus HA antigen with a test serum, both of which have been previously diluted with the above-described diluent for rubella virus HA antigen and for test serum and, then, admixing the resultant mixture further with a suspension of erythrocytes diluted with the above-mentioned diluent for erythrocytes to assess the agglutination or non-agglutination of the erythrocytes. By this method is it possible to determine the titer of rubella virus HI antibody in the test serum with accuracy and high sensitivity.

To perform the HI reaction according to this invention, use may be made of any procedure, a typical procedure being by the microtiter method. Such a procedure, for example, comprises taking 0.025 ml. of a test serum whose non-specific inhibitors of agglutination have been removed or inactivated, diluting it serially in two-fold steps on a micro-plate with the above-mentioned diluent for rubella HA antigen and for test serum, and adding 0.025 ml. of a rubella HA antigen fluid previously diluted to 4 HA units with the same diluent. Then, after 60 minutes' standing at room temperature, the mixture is further admixed with 0.050 ml. of a 0.25% suspension of erythrocytes previously diluted with the aforementioned diluent for erythrocytes. The entire mixture is allowed to stand at 4° C for 60 minutes and, then, examined for the agglutination or non-agglutination of the erythrocytes. The rubella virus HI antibody titer is expressed in terms of the maximum dilution factor of the test serum at which the agglutination of erythrocytes has been completely inhibited.

This invention, in another aspect thereof, provides a kit for the above-mentioned rubella virus HI test, which comprises (1) the said new diluent for rubella virus HA antigen and for rubella virus HI test sera, (2) the said diluent for erythrocytes and (3) rubella virus HA antigen. This kit may further comprise the erythrocytes, particularly, the fixed erythrocytes.

The following Examples and Experimentals are merely intended to illustrate a presently preferred embodiment of this invention and not to restrict the scope of this invention.

Throughout the present specification as well as in claims, the "mg.", "g.", "ml.", "° C", "M" and "N" respectively refer to "milligram(s)", "gram(s)", "milliliter(s)", "degrees centigrade", "molar concentration" and "normality", and percentages are weight/volume unless otherwise specified.

EXAMPLE 1

| | |
|---|---|
| HEPES | 594 mg. |
| NaCl | 4.09 g. |
| Bovine serum albumin | 1.0 g. |

The above components are dissolved in 450 ml. of distilled water, adjusted to pH 6.2 with 0.1N-NaOH and made up to 500 ml. with a further amount of distilled water. By the above procedure there is obtained a diluent for rubella virus HA antigen and for test sera for use in rubella virus HI test, which contains 0.005 M-HEPES, 0.14M-NaCl and 0.2% of bovine serum albumin and is of pH 6.2.

EXAMPLE 2

| | |
|---|---|
| HEPES | 2.97 g. |
| $CaCl_2$ (anhydrous) | 111 mg. |
| NaCl | 4.09 g. |
| Gelatin | 25 mg. |

The above components are dissolved in 450 ml. of distilled water, adjusted to pH 6.2 with 1N-NaOH and made up to 500 ml. with a further amount of distilled water to prepare a diluent for erythrocytes, which contains 0.025M-HEPES, 0.002M-$CaCl_2$, 0.14M-NaCl and 0.005% of gelatin and is of pH 6.2.

Experimental 1

Portions of a rubella virus HA antigen were dissolved in the diluent of Example 1 for rubella virus HA antigen and test sera and in a conventional diluent, HSAGC[1], respectively. Aliquots of each antigen fluids were stored at 5° C and room temperature (25° C), respectively, and samples taken at timed intervals were assayed for HA titers to compare the relative stability of the HA antigen dilutions.

The HA titers were determined in the following manner. Thus, the formalinized erythrocytes of one-day-old chicks (a suspension in distilled water of the lyophilized erythrocytes obtained by the procedure of Example 1 of Japanese Patent Publication No. 37724/1975; the same hereinafter) were diluted with the diluent of Example 2 for erythrocytes and the rubella virus HA titer was determined by Sever's microtiter method on a permanent V-plate (Journal of Immunology 88, 320–329(1962)). The dilution of the HA antigen was performed using the diluent of Example 1.

Table 1

| HA antigen fluid stored | Storage temperature | Rubella virus HA titer Storage time | | | |
|---|---|---|---|---|---|
| | | 0 hr. | 1 hr. | 2 hrs. | 4 hrs. |
| Diluent of Example 1 | 5° C | 64 | 64 | 64 | 32 |
| | Room temperature | 64 | 64 | 128 | 64 |
| HSAGC[1] | 5° C | 64 | 8 | 4 | <4 |
| | Room temperature | 64 | 16 | 8 | 4 |

[1]HSAGC stands for HEPES-Saline-Albumin-Gelatin-$CaCl_2$, the composition of which is particularized below.

| | |
|---|---|
| HEPES | 2.97 g. |
| NaCl | 4.09 g. |
| Bovine serum albumin | 1.0 g. |
| Gelatin | 1.25 mg. |
| $CaCl_2$ (anhydrous) | 55.5 mg. |

The above components were dissolved in distilled water, adjusted to pH 6.2 with 1N-NaOH and made up to 500 ml. with distilled water.

Experimental 2

Aliquots of a test human serum were each subjected to one of the following pretreatments (a) to (e) to prepare seral samples for rubella virus HI tests.

a. Untreated control serum

To 0.1 ml. of human serum was added 0.3 ml. of HS[*2].

b. Kaolin-treated serum

To 0.1 ml. of human serum was added 0.3 ml. of HS, followed by addition of 0.4 ml. of 25% kaolin-HS suspension to the resultant serum dilution. The mixture was incubated at 30° C for 30 minutes, at the end of which time it was centrifuged. The supernatant fluid was taken and heated at 56° C for 30 minutes to inactivate the serum.

c. Acetone-treated serum

To 0.1 ml. of human serum was added about 4 ml. of acetone and the mixture was centrifuged at 1500 r.p.m. for 5 minutes. The supernatant fluid was discarded and, following addition of about 4 ml. of acetone, the mixture was similarly centrifuged again. The supernatant was discarded. The sediment was dried and 0.4 ml. of HS was added. The mixture was allowed to stand at 4° C overnight and, then, heated at 56° C for 30 minutes to inactivate the serum.

d. Heparin-$MnCl_2$-treated serum

To 0.1 ml. of human serum was added 0.2 ml. of HS, followed by addition of 0.05 ml. each of heparin (1,000 units/ml.) and 0.5M-$MnCl_2$. The mixture was allowed to stand at 4° C for 60 minutes and centrifuged. The supernatant fluid was taken and heated at 56° C for 30 minutes to inactivate the serum.

e. Phospholipase C-treated serum

To 0.1 ml. of human serum was added 0.2 ml. of HS, followed by addition of 0.1 ml. of 0.06 units/ml. of phospholipase C[*3]. The mixture was incubated at 37° C overnight and, then, heated at 56° C for 30 minutes to inactivate the serum.

[*2] HS stands for HEPES-Saline, the composition of which is as follows. HEPES:—238 mg. NaCl:—4.09 g.

The above components were dissolved in 450 ml. of distilled water, adjusted to pH 7.2 with 0.1N-NaOH and made up to 500 ml. with distilled water.

[*3]. The phospholipase C used is a commercial product prepared from Clostridium perfringens ("Phospholipase C" prepared and sold by P-L Biochemicals, Inc., Milwaukee, U.S.A.), one unit of this enzyme being capable of liberating 1 micromole of the acid-soluble phosphorus (phosphorus of phosphorylcholine) per minute when allowed to act upon lecithin at pH 7.3 and 37° C.

To each of the various HI test serum samples obtained as above was added 0.1 ml. of a 10% suspension of the formalinized erythrocytes of one-day-old chicks, whereby the naturally-occurring agglutinins were absorbed before conducting an HI test.

In this HI test, using the diluent of Example 1 for the dilution of serum and antigen and the diluent of Example 2 for the dilution of formalinized erythrocytes, the rubella virus HI antibody titer was determined by the above-mentioned Sever's microtiter method on a permanent V-plate. The results are set forth in Table 2.

Table 2

| Test serum No. | Rubella virus HI antibody titer | | | | |
|---|---|---|---|---|---|
| | Untreated | Kaolin-treated | Acetone-treated | Heparin-$MnCl_2$-treated | Phospholipase C-treated |
| 1 | 640 | 16 | 20 | 40 | 40 |

Table 2-continued

| Test serum No. | Rubella virus HI antibody titer | | | | |
|---|---|---|---|---|---|
| | Untreated | Kaolin-treated | Acetone-treated | Heparin-$MnCl_2$-treated | Phospholipase C-treated |
| 2 | 640 | 32 | 40 | 40 | 80 |
| 3 | 640 | 16 | 40 | 20 | 40 |
| 4 | 640 | 16 | 20 | 20 | 20 |
| 5 | 320 | 8 | 5 | 10 | 5 |
| 6 | 320 | 16 | 20 | 20 | 20 |
| 7 | 640 | 16 | 20 | 40 | 40 |
| 8 | 640 | 16 | 20 | 40 | 40 |
| 9 | 1280 | 16 | 40 | 80 | 80 |
| 10 | 640 | <8 | 5 | <5 | <5 |
| 11 | 640 | 64 | 40 | 40 | 80 |
| 12 | 1280 | 64 | 80 | 160 | 160 |
| 13 | 1280 | 64 | 40 | 80 | 80 |
| 14 | 640 | 32 | 40 | 40 | 40 |
| 15 | 640 | <8 | <5 | <5 | <5 |

Experimental 3

Aliquots of a rubella virus HA antigen were diluted with the diluent of Example 1 and HSAGC, respectively, to an HA titer of 4 units and stored at 5° C for 2 hours. Using each of thus-diluted and stored HA antigen fluids, the rubella virus HI antibody titer was determined for the phospholipase C-treated sera of Experimental 2 in the same manner as in Experimental 2. Where the HA antigen fluids diluted with the diluent of Example 1 were employed, the test sera were diluted with the diluent of Example 1 while the formalinized erythrocytes were diluted with the diluent of Example 2. Where the HA antigen diluted with HSAGC was employed, both the serum and formalinized erythrocytes were diluted with HSAGC. The results obtained are set forth in Table 3.

Table 3

| Test serum No. | Rubella virus HI antibody titer | |
|---|---|---|
| | HA antigen diluted with the diluent of Example 1 | HA antigen diluted with HSAGC |
| 1 | 40 | 80* |
| 2 | 80 | 80* |
| 3 | 40 | 80* |
| 4 | 20 | 40* |
| 5 | 5 | 10* |
| 6 | 20 | 20* |
| 7 | 40 | 40* |
| 8 | 40 | 80* |
| 9 | 80 | 320* |
| 10 | <5 | <5 |
| 11 | 80 | 160* |
| 12 | 160 | 160* |
| 13 | 80 | 80* |
| 14 | 40 | 160* |
| 15 | <5 | <5 |

*Because of the inactivation of HA antigen during storage (a reduction in HA titer from 4 units to 1 unit), no adequate erythrocyte agglutination pattern was obtained. This meant an ill-defined end-point of the HI reaction, which interferred with an accurate assessment of the HI titer.

*Because of the inactivation of HA antigen during storage (a reduction in HA titer from 4 units to 1 unit), no adequate erythrocyte agglutination pattern was obtained. This meant an ill-defined end-point of the HI reaction, which interferred with an accurate assessment of the HI titer.

What is claimed is:

1. A diluent for rubella virus hemagglutinating antigen and for rubella virus hemagglutination-inhibition test sera, which contains N-2-hydroxyethylpiperazine-N'-2'-ethanesulfonic acid in a molar concentration from about 0.001 to about 0.01 and NaCl, the pH of which is in the range of about 6.0 to about 7.5, and which is free from calcium ion.

2. A diluent as claimed in claim 1, wherein the molar concentration of N-2-hydroxyethylpiperazine-N'-2'-ethanesulfonic acid is in the range of about 0.004 to about 0.006.

3. A diluent as claimed in claim 1, which is in the pH range of about 6.0 to about 6.5.

4. A diluent as claimed in claim 1, which further contains albumin.

5. A diluent as claimed in claim 4, wherein the albumin is serum albumin.

6. A diluent as claimed in claim 4, wherein the albumin is in a concentration from about 0.05 to about 1 percent.

7. A diluent as claimed in claim 1, wherein the molar concentration of NaCl is in the range of about 0.05 to about 0.3.

8. A method for rubella virus hemagglutination-inhibition test, which comprises admixing a test serum previously diluted with a diluent which contains N-2-hydroxyethylpiperazine-N'-2'-ethanesulfonic acid in a molar concentration from about 0.001 to about 0.01 and NaCl, the pH of which is in the range of about 6.0 to about 7.5 and which is free from calcium ion with rubella virus hemagglutinating antigen previously diluted with the said diluent and, then, admixing the resultant mixture with a suspension of erythrocytes previously diluted with a diluent which contains N-2-hydroxyethylpiperazine-N'-2'-ethanesulfonic acid in a molar concentration from about 0.01 to about 0.05, $CaCl_2$ in a molar concentration from about 0.0005 to about 0.01 and NaCl and the pH of which is in the range of about 6.0 to about 6.5 to assess agglutination or nonagglutination of the erythrocytes.

9. A method as claimed in claim 8, wherein the diluent for rubella virus hemagglutinating antigen and for test serum further contains albumin.

10. A method as claimed in claim 8, wherein the diluent for erythrocytes further contains gelatin.

11. A method as claimed in claim 8, wherein the test serum is human serum.

12. A method as claimed in claim 8, wherein the erythrocytes are fowl erythrocytes.

13. A method as claimed in claim 12, wherein the fowl is chick.

14. A method as claimed in claim 8, wherein the erythrocytes are fixed erythrocytes.

15. A diluent as claimed in claim 3, which has a pH of about 6.2.

16. A diluent as claimed in claim 7, wherein the molar concentration of NaCl is in the range of about 0.14 to about 0.15.

* * * * *